(12) United States Patent
Puttler et al.

(10) Patent No.: US 8,535,580 B2
(45) Date of Patent: Sep. 17, 2013

(54) DIGITALLY FORMING A DENTAL MODEL FOR FABRICATING ORTHODONTIC LABORATORY APPLIANCES

(75) Inventors: Oliver L. Puttler, La Crescenta, CA (US); Sunghan Kim, Montebello, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 282 days.

(21) Appl. No.: 12/670,132

(22) PCT Filed: Sep. 9, 2008

(86) PCT No.: PCT/US2008/075658
§ 371 (c)(1),
(2), (4) Date: Jan. 22, 2010

(87) PCT Pub. No.: WO2009/042378
PCT Pub. Date: Apr. 2, 2009

(65) Prior Publication Data
US 2010/0219546 A1    Sep. 2, 2010

Related U.S. Application Data

(60) Provisional application No. 60/975,687, filed on Sep. 27, 2007.

(51) Int. Cl.
*A61C 13/00* (2006.01)
(52) U.S. Cl.
USPC .......................................................... 264/16
(58) Field of Classification Search
USPC .......................................................... 264/16
See application file for complete search history.

(56) References Cited

U.S. PATENT DOCUMENTS

| | | | |
|---|---|---|---|
| 2,531,222 | A | 11/1950 | Kesling |
| 3,271,858 | A | 9/1966 | Simmons |
| 3,994,068 | A | 11/1976 | Goshgarian |
| 4,436,684 | A | 3/1984 | White |
| 4,672,032 | A | 6/1987 | Slavkin et al. |
| 4,798,534 | A | 1/1989 | Breads |
| 4,976,614 | A | 12/1990 | Tepper |

(Continued)

FOREIGN PATENT DOCUMENTS

| | | |
|---|---|---|
| EP | 0 097 001 | 12/1983 |
| EP | 1 570 803 | 9/2005 |

(Continued)

OTHER PUBLICATIONS

Sassani et al., "Computer-Assisted Fabrication of Orthodontic Appliances: Considering the Possibilities", J. of American Dental Assoc., vol. 126, Sep. 1995, pp. 1296-1300.

(Continued)

*Primary Examiner* — Larry Thrower
(74) *Attorney, Agent, or Firm* — Philip P. Soo (57) ABSTRACT

The present invention provides a method that uses digital data, such as that obtained from an intraoral scanner, to fabricate a wide range of customized laboratory appliances. The digital data is used to form a negative mold, which is in turn used to make a physical dental model. The negative mold is configured such that it can be flexed, stretched, fractured or disassembled to release the physical dental model. The physical dental model is then used for fabricating an orthodontic laboratory appliance.

15 Claims, 5 Drawing Sheets

(56) References Cited

U.S. PATENT DOCUMENTS

| | | | |
|---|---|---|---|
| 5,204,055 | A | 4/1993 | Sachs et al. |
| 5,340,656 | A | 8/1994 | Sachs et al. |
| 5,387,380 | A | 2/1995 | Cima et al. |
| 5,490,882 | A | 2/1996 | Sachs et al. |
| 5,490,962 | A | 2/1996 | Cima et al. |
| 5,518,680 | A | 5/1996 | Cima et al. |
| 5,700,289 | A | 12/1997 | Breitbart et al. |
| 6,210,162 | B1 | 4/2001 | Chishti et al. |
| 6,217,334 | B1 | 4/2001 | Hultgren |
| 6,227,851 | B1 | 5/2001 | Chishti et al. |
| 6,394,801 | B2 | 5/2002 | Chishti et al. |
| 6,398,548 | B1 | 6/2002 | Muhammad et al. |
| 6,497,574 | B1 | 12/2002 | Miller |
| 6,540,512 | B1 | 4/2003 | Sachdeva et al. |
| 6,554,611 | B2 | 4/2003 | Chishti et al. |
| 6,612,143 | B1 | 9/2003 | Butscher et al. |
| 6,648,640 | B2 | 11/2003 | Rubbert et al. |
| 6,821,462 | B2 | 11/2004 | Schulman et al. |
| 6,928,733 | B2 | 8/2005 | Rubbert et al. |
| 7,076,980 | B2 | 7/2006 | Butscher et al. |
| 7,134,874 | B2 | 11/2006 | Chishti et al. |
| 7,435,084 | B2 | 10/2008 | Liu et al. |
| 2003/0116299 | A1* | 6/2003 | Embert et al. ............ 164/4.1 |
| 2003/0207227 | A1 | 11/2003 | Abolfathi |
| 2005/0040551 | A1* | 2/2005 | Biegler et al. ............ 264/19 |

FOREIGN PATENT DOCUMENTS

| | | |
|---|---|---|
| JP | 59-151953 | 8/1984 |
| JP | 09-159419 | 6/1997 |
| JP | 2004-306473 | 11/2004 |
| JP | 2007-125113 | 5/2007 |
| WO | WO 2005/115266 | 12/2005 |

OTHER PUBLICATIONS

Jost-Brinkmann et al., "Computer-Aided Fabrication of Bonded Lingual Retainers", J. Clinical Orthodontics, vol. XXX, No. 10, 1996, pp. 559-563.

PCT/US2008/075658 International Search Report, Oct. 11, 2008.

Willison, Practical Guide to Orthodontic Appliances: a comprehensive resource from theory to fabrication, Tonawanda, New York, Great Lakes Orthodontics, pp. 593-599; 2004.

\* cited by examiner

DIGITALLY FORMING A DENTAL MODEL FOR FABRICATING ORTHODONTIC LABORATORY APPLIANCES

CROSS REFERENCE TO RELATED APPLICATIONS

This application is a national stage filing under 35 U.S.C. §371 of PCT/US2008/075658, filed Sep. 9, 2008, which claims priority to U.S. Provisional Application Ser. No. 60/975,687, filed Sep. 27, 2007, the disclosure of which is incorporated by reference in its/their entirety herein.

BACKGROUND OF THE INVENTION

1. Field of the Invention

This invention relates to the area of digital orthodontics and more particularly to methods of using digital data to fabricate appliances.

2. Description of the Related Art

Orthodontics is the area and specialty of dentistry associated with the supervision, guidance and correction of malpositioned teeth into proper locations. Orthodontic treatment can be useful in correcting defects in a patient's bite (also called occlusion) along with promoting better hygiene and improving the overall aesthetics and health of the teeth.

During the course of such treatment, an orthodontic professional may direct the patient to wear a customized laboratory appliance to achieve a particular treatment goal. For example, such an appliance may be needed to reposition the patient's mandible or expand the palatal arch. Other laboratory appliances, such as Hawley retainers, are very commonly prescribed to provide tooth immobilization at the conclusion of treatment. These laboratory appliances are typically fabricated using a labor intensive process carried out by a skilled technician. Early appliances were hand crafted by practitioners on a physical dental model made from plaster, or orthodontic stone. The physical dental models, in turn, were typically cast from an impression of a patient's dentition made from a suitable impression material, such as alginate or polyvinylsiloxane (PVS). Techniques of dental mold making are well known.

Today, laboratory appliance providers such as commercial dental laboratories continue to produce these appliances by applying and shape setting plastic and/or custom bent wires to an orthodontic stone model of the patient's dental structure. When a laboratory appliance is needed, a stone model can be prepared using standard dental impressions taken at the site of an orthodontic (or dental) professional and then the model transported by mail to the dental laboratory along with an order form to request the fabrication of a laboratory appliance. While this workflow is effective, transporting the physical dental model to the laboratory incurs a delay as well as a shipping cost. Moreover, the process of creating an alginate impression and pouring a stone model is time consuming for the staff of an orthodontic practice and is often unpleasant for the patient.

The preparation of impressions followed by the casting of stone models and the shipment of stone models to an orthodontic or dental laboratory to manufacture a laboratory appliance remains a largely manual process. A method which improves upon the efficiency and reliability of current methods would be welcome by both orthodontic professionals and appliance fabricators.

SUMMARY OF THE INVENTION

The present invention provides a method that uses digital data, such as that obtained from an intraoral scanner, to fabricate a wide range of laboratory appliances for the orthodontic professional. The present invention achieves this by providing methods that use digital data to directly or indirectly form a negative physical model, or negative mold. This negative mold is, in turn, used to make a physical dental model for fabricating orthodontic laboratory appliances.

In one aspect, the present invention is directed to a method of fabricating an orthodontic laboratory appliance that includes obtaining digital data representing at least a portion of a patient's dental structure, forming a negative mold using the digital data, making a physical dental model from the negative mold, moving at least two sections of the negative mold away from each other in order to release the physical dental model from the negative mold, and fabricating the laboratory appliance from the physical dental model. In another aspect, the invention is directed to a method of fabricating an orthodontic laboratory appliance comprising obtaining digital data representing at least a portion of a patient's dental structure, forming a negative mold using the digital data, making a physical dental model from the negative mold, and flexibly removing the negative mold from the physical dental model, and fabricating the laboratory appliance from the physical dental model.

Optional aspects of the invention include (a) additionally creating a positive mold using the digital data, wherein the act of forming the negative mold is carried out using the positive mold, (b) using a negative mold having a frangible line of weakness to allow mold sections to be fractured from each other, and (c) heating the negative mold in order to flexibly separate the negative mold from the physical dental model. Another optional aspect includes a negative mold that is formed as an assembly of mold sections, where each mold section is subsequently released from the physical dental model without interference.

BRIEF DESCRIPTION OF THE DRAWINGS

FIG. 7a shows a perspective view of the negative dental mold according to another embodiment of the invention;

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

Detailed Description of the Preferred Embodiments

As used herein, orthodontic laboratory appliances include patient-customized appliances such as orthodontic retainers, occlusal splints, palatal expanders, mouthguards, functional appliances and Herbst appliances, and appliances to relieve sleep apnea. These appliances can be used to provide tooth immobilization, occlusal protection, relief of temporomandibular joint disorder (TMD) symptoms, repositioning of the mandible, palatal arch expansion, and other dental/skeletal therapeutic actions as well as to provide for certain steps in orthodontic treatment. Orthodontic laboratory appliances differ from mass-produced orthodontic appliances such as brackets in that orthodontic laboratory appliances are fabricated using a physical model that represents the shape of the patient's teeth in either actual or desired positions.

A step-by-step process that begins with collecting digital data representing a patient's dental structure and ends with the fabrication of a customized laboratory appliance, is presented herein and organized under five broad headings: obtaining digital data, forming a negative mold, making a physical dental model, releasing the physical dental model, and fabricating a laboratory appliance. A more detailed presentation of the steps according to various embodiments is further illustrated in the flowchart shown in FIG. 1. Each of these steps will be particularly explained within the framework of the headings which follow.

Obtaining Digital Data

Figure 1:
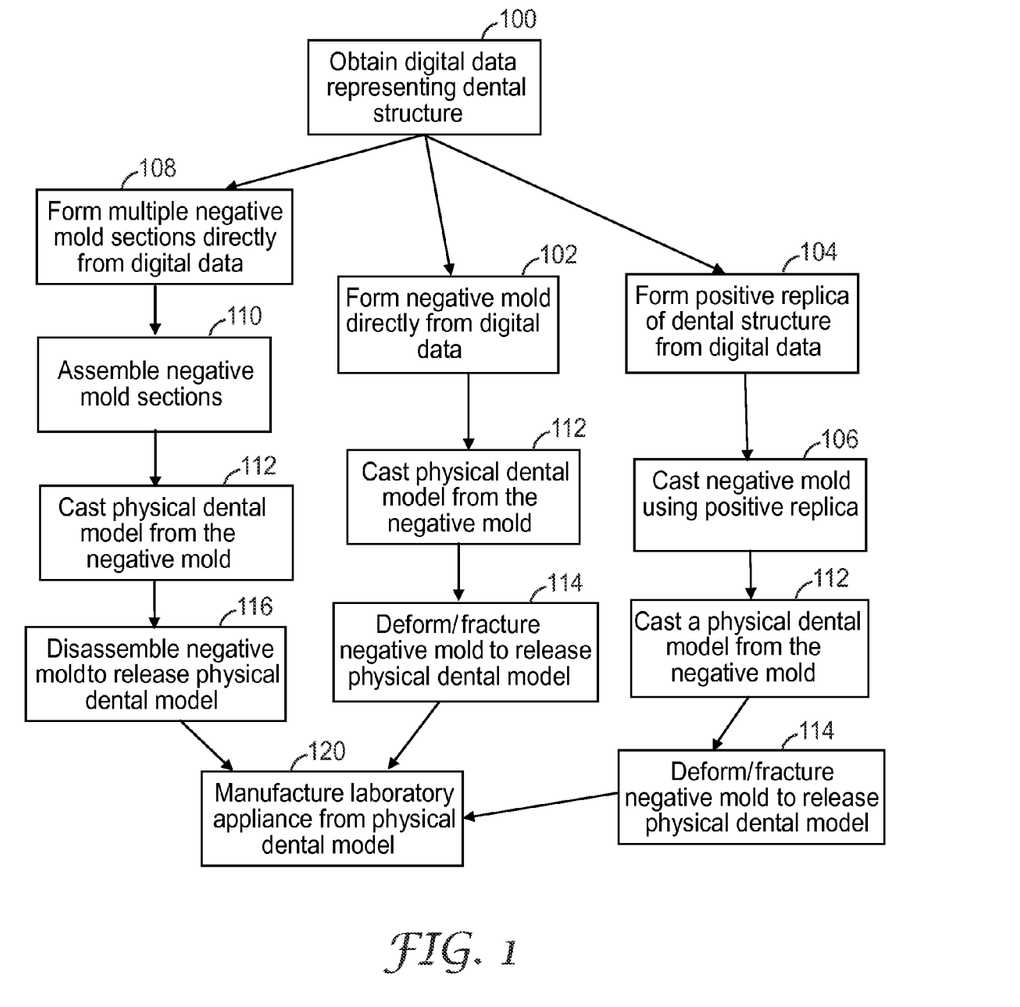
FIG. 1 shows a flowchart outlining steps used in exemplary embodiments of the invention.

In the first step, designated as block 100 in FIG. 1, digital data representing a three dimensional (3D) image of a patient's dental structure is obtained. The digital data may represent the entire dental structure of a patient, just the upper or lower arch, or only a portion of one or both arches. Digital data representing only a portion of a patient's dental structure may be desired, for example, in cases where the desired laboratory appliance engages some but not all of the teeth. In some embodiments, the digital data may be obtained using a hand-held intra-oral scanner such as the intra-oral scanner using active wavefront sampling developed by Brontes Technologies, Inc. (Lexington, Mass.). Alternatively, other intra-oral scanners or intra-oral contact probes may be used. As another option, the digital data file may be obtained by scanning an impression of the patient's teeth. As still another option, the digital data may be obtained by scanning a physical model of the patient's teeth or by using a contact probe on a model of the patient's teeth. The model used for scanning may be made by pouring a casting material (such as orthodontic stone or epoxy resin) into an impression of the patient's teeth and allowing the casting material to cure. Any suitable scanning technique may be used for scanning the model, such as X-ray, laser, computed tomography (CT), and magnetic resonance imaging.

Forming a Negative Mold

In a following step, designated as block 102 in FIG. 1, the digital data is processed as needed and then used in conjunction with rapid prototyping or milling techniques to form a negative mold. Examples of "rapid prototyping" techniques include, but are not limited to, three-dimensional (3D) printing, selective area laser deposition or selective laser sintering (SLS), electrophoretic deposition, robocasting, fused deposition modeling (FMD), laminated object manufacturing (LOM), stereolithography (SLA) and photostereolithography. Issued U.S. Pat. Nos. 5,340,656, 5,490,882, 5,204,055, 5,518,680, 5,490,962, 5,387,380, 5,700,289, 5,518,680, and 4,672,032 describe examples of suitable rapid prototyping techniques. Particularly suitable rapid prototyping machines include the VIPER brand SLA system from 3D Systems (Rock Hill, S.C.) or EDEN brand 500V printer from Objet Geometries Ltd. (Rehovot, ISRAEL). As another option, one could use CAD-CAM software to direct a milling machine or similar device to fabricate the negative mold.

Figure 2:
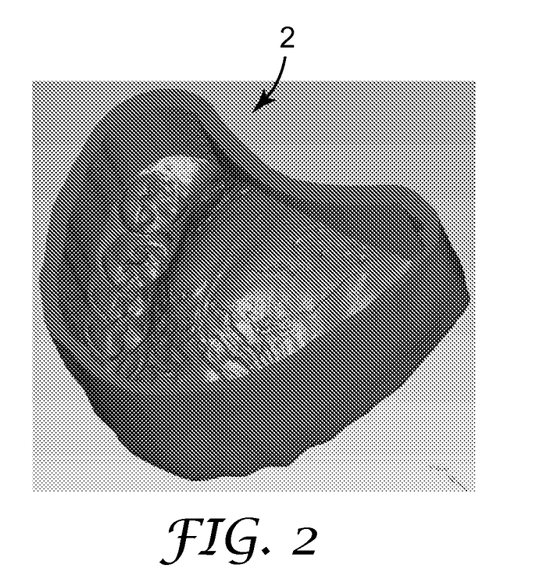
FIG. 2 shows a negative mold according to one embodiment of the invention, showing inner surfaces of the mold that conform to a dental structure.
Figure 3:
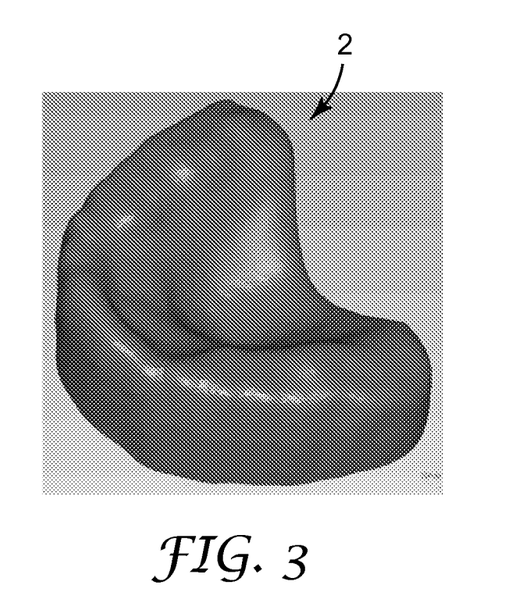
FIG. 3 shows the negative mold of FIG. 2 looking towards the outer surfaces of the mold.

Optionally, the raw digital data file of the dental structure may be initially "cleansed" by removing any data points that represent clear error or are unnecessary. For example, data files representing a tooth surface that include a data point significantly outside the normal expected geometrical relationship of adjacent data points could be fixed by data handling software to remove the erroneous data point. In addition, tooth data points that are missing could be added or estimated by data handling software to create realistic, smoothly curved tooth shapes, defined by the data points. In some embodiments, the digital data may be converted from digital point clouds to 3D surfaces by means of software by a provider such as Geomagic, Inc. (Triangle Park, N.C.). Once this conversion is completed, the digital data set defining the dental structure may then be used to rapid prototype or mill a corresponding three dimensional negative mold. FIGS. 2 and 3 show two views of an exemplary negative mold 2 looking towards the interior occlusal surfaces and exterior surfaces, respectively. The walls of the negative mold 2 are defined with sufficient thickness to provide adequate structural strength while retaining enough flexibility to facilitate subsequent removal of a casting that is made using mold 2. Optionally the walls of the mold 2 may include ribs or other reinforcing structures to prevent inadvertent distortion of the mold 2. Examples of suitable wall thicknesses for the negative mold 2 range from 0.25 millimeters to 10 millimeters, depending upon the stiffness of the mold material. If the negative mold 2 is very soft, then higher wall thicknesses may be required.

In exemplary embodiments, the negative mold 2 is directly printed using rapid prototyping or milling techniques. Preferably, the negative mold 2 should have a smooth surface finish after printing and accurately replicate the contours of the original dental structure. Preferably, the negative mold 2 is formed from a flexible matrix material. In some embodiments, the matrix material has a Shore Scale A hardness that is in the range of 2 to 90 and displays an elongation to break that ranges from 30% to 1000%.

An alternative method to forming the negative mold 2 is provided by blocks 104 and 106 in FIG. 1. In the approach provided by blocks 104 and 106, a positive physical model or positive mold of the dental structure is created using the digital data and the negative mold 2 subsequently formed using the positive mold, respectively. As described earlier, the positive mold can be prepared using rapid prototyping techniques or using other methods such as computerized numerical control (CNC) milling or the like. The subsequent forming of the negative mold 2 may then be achieved using a casting process, in which a tray molding vessel is filled with a flowable matrix material, the positive mold inverted and placed in the molding vessel, and the matrix material solidified to form the negative mold. Optionally, the molding vessel has an overall arcuate shape with a U-shaped channel, such as those used for dental impressions. A primary advantage to forming the negative mold using an intermediate positive mold is the freedom to use a wider array of low modulus materials to form the negative mold. An example of a low modulus material is Z-DUPE brand duplication silicone provided by Henry-Schein Inc. (Melville, N.Y.). Also advantageous is the ability to use a wide array of rapid prototyping materials and processes to create the positive mold. This workflow is not limited to the varieties of resins available for rapid prototyping techniques. For example, the negative mold 2 may be advantageously cast from low modulus resins that may be more flexible and/or better suited for molding than those currently used in 3D printing machines. Since a relatively soft matrix material is used to cast the negative mold, the walls of the negative mold 2 should be shaped or formed sufficiently thick to prevent undue deformation of the mold under the weight of the model matrix material as the physical dental model (to be identified later, in FIG. 8) is cast.

Other methods of forming negative mold 2 from the positive mold are also possible. For example, the negative mold 2 can be formed from a sheet of polymer which is vacuum formed over the positive mold. Suitable materials include polycarbonate sheets such as Makrolon brand material from Bayer or Lexan brand polycarbonate from GE having a thickness of 1.52 millimeters (0.06 inch). Other materials, such as polyethyleneterephthalate glycol ("PETG") may also be used. If this method is used, heat is optionally applied during the vacuum forming process in order to facilitate conformance of the sheet to the positive mold.

Figure 5:
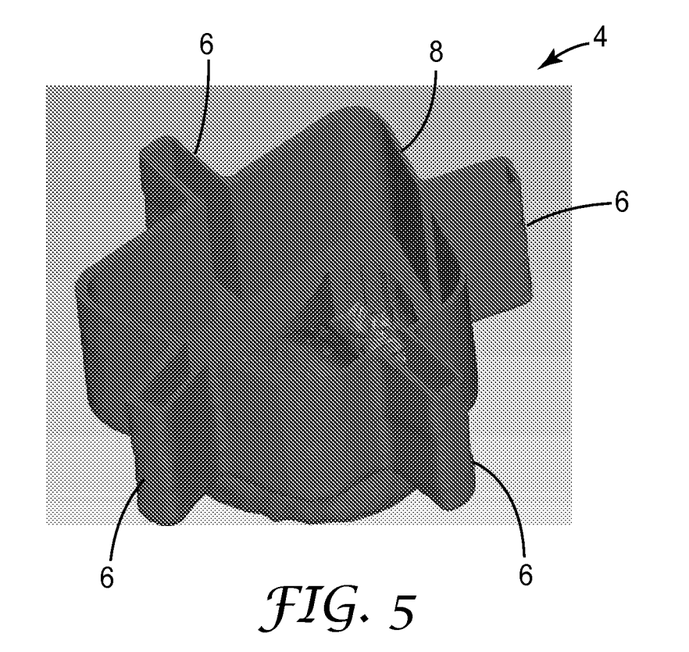
FIG. 5 shows a perspective view of a negative dental mold with features to facilitate release from the physical dental model.

Although not shown, the negative mold 2 may optionally include features that assist in the removal of the physical dental model. For example, the negative mold 2 may include at least one notch, perforation, or groove that extends along portions of the mold to define a line (or lines) of weakness to help initiate fracture of the negative mold 2 and facilitate release from the physical dental model. Optionally, the notch or groove is located on the exterior surface of the mold 2 and allows the mold 2 to be easily peeled away in two or more sections (e.g. like a banana) from the physical dental model. Optionally, and as shown in FIG. 5, the mold 2 includes four handles 6 that extend outwardly from the mold body 8 and provide a purchase point for a user to grasp and apply force to the edge of the mold body 8 and facilitate disengagement of the mold 4 from the physical dental model. The number and configuration of handles 6 in FIG. 5 is clearly exemplary only and myriad other handles to provide a mechanical aid are also possible.

Figure 6:
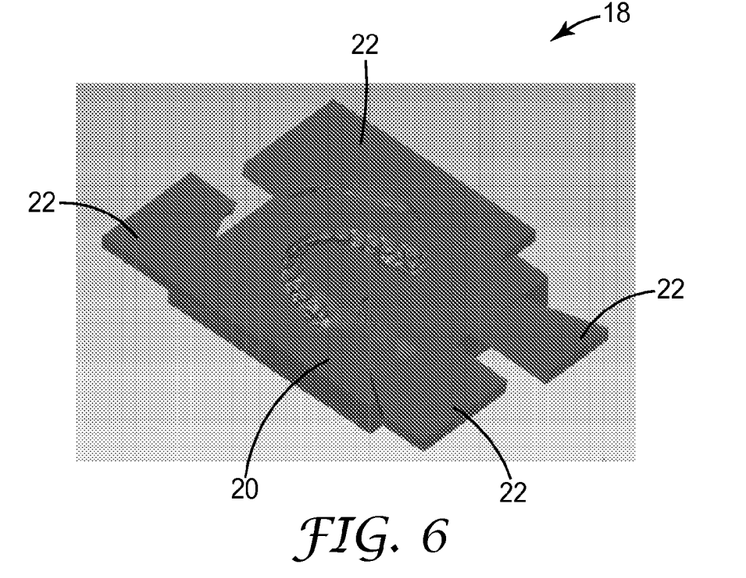
FIG. 6 shows a perspective view of a negative dental mold that has been disassembled according to another embodiment of the invention.
Figure 7:
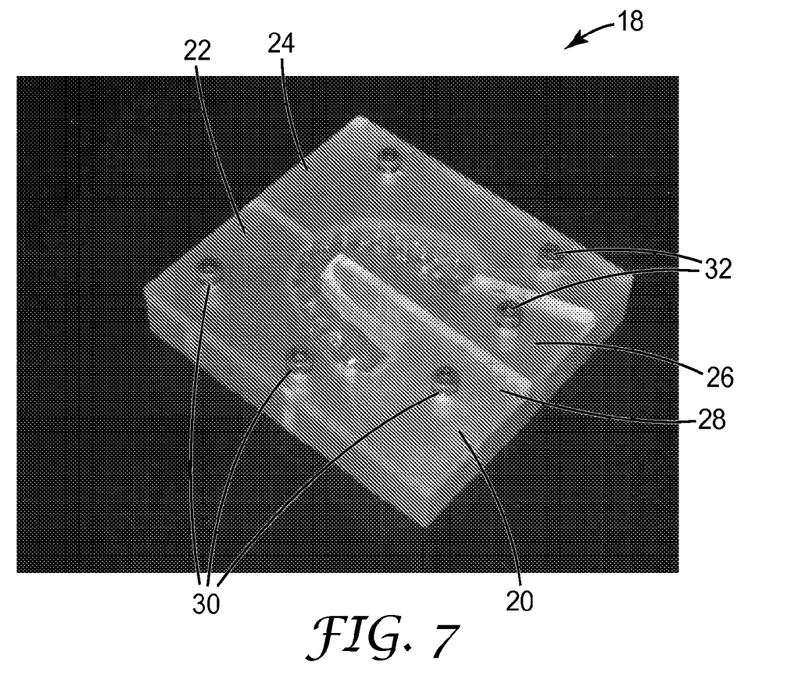
FIG. 7 shows a perspective view of the negative dental mold shown in FIG. 6 as assembled.

In a third embodiment, provided by blocks 108 and 110 of FIG. 1, two or more mold sections are formed from the digital data are then assembled to form the negative mold, respectively. This approach is illustrated by FIGS. 6 and 7, which show an exemplary negative mold 18 in disassembled and assembled form, respectively. As shown, mold 18 includes five mold sections 20,22,24,26,28. Mold sections 20,22,24, 26,28 are configured to form the negative mold 18 when assembled. Preferably, mold sections 20,22,24,26,28 are individually formed by rapid prototyping or milling methods. In another embodiment, the negative mold 18 is formed as a unitary component, cut into sections 20,22,24,26,28, and reassembled to form the negative mold 18 prior to casting the physical dental model. If this approach is taken, however, it is preferable to minimize the amount of mold material lost as a result of the cutting process, since this directly affects the shape of the mold when reassembled. To assist with proper registration of mold sections 20,22,24,26,28, the mold section 20 is registered with the mold sections 22,24,26,28 using coupling pins 32. Optionally, it is possible to use a tab, rail or any other mechanical alignment guide that extends through at least part of the negative mold to prevent unwanted sliding of the mold sections 20,22,24,26,28 relative to each other. Each of the sections 20,22,24,26,28 is also individually configured so that there are no undercuts that would hinder subsequent release from a casting. Consequently, after the physical dental model is cast and hardened in the negative mold 18, each mold section can be individually separated from the model without interferences. The coupling pins 32 not only align the mold sections but tightly secure the sections to each other to form an adequate seal against leakage from the mold 18 during the casting of the physical dental model. In the embodiment shown, coupling pin 32 is a screw-type coupling, although other fastening means are also possible.

FIG. 7a shows an exemplary negative mold 50 according to a fourth embodiment of the invention. The negative mold 50 is generally "U"-shaped and includes a mold body 51 and a support structure 52 connected to the mold body 51. The support structure 52 enhances the stiffness of the mold 50 thereby preventing undue deflection or distortion of the mold body 51 when the mold 50 is used to cast the physical dental model (to be described in the next section). Optionally and as shown in this example, the support structure 52 includes a rim 53 extending along the gingival edges of the mold body 51. A seam 56 separates the rim 53 and the mold body 51. The rim 53 optionally has a facial-lingual thickness greater than the walls of the mold body 51 to provide enhanced stiffness. The support structure 52 can also be formed from a material with a higher stiffness, Shore hardness, or modulus than that of the mold body 51 for greater stiffening effect.

The support structure 52 in FIG. 7a further includes an elongated bridge member 54 extending parallel to the occlusal plane of the arch and connected to two or more spaced apart locations along the mold body 51 thereby mechanically reinforcing the mold 50. In the example shown, the bridge member 54 is generally "T"-shaped and connects the lingual-facing posterior portions of the mold 50 as well as the lingual-facing anterior portion of the mold 50 to one other. Although the combination is shown in FIG. 7a, the bridge member 54 and the thickened rim 53 can also be used independently to stiffen the mold 50. The mold body 51 and support structure 52 may be fabricated either integrally or separately using the rapid prototyping methods previously mentioned.

As set out above, it is advantageous to use a negative mold (such the mold 2,4,18,50) that can be flexed, deformed, softened, fractured, or disassembled to facilitate removal of a cast dental model. This is particularly notable because the crown of a human tooth tends to have an overall wedge shape when looking at the tooth from the facial or lingual direction (i.e. looking from the cheeks/lips towards the tongue and vice-versa). In other words, the occlusal portion of the crown is larger than the gingival portion of the crown for many of the teeth in a patient's dentition. Because teeth have this wedge shaped characteristic, there are undercuts and interferences that would render removal of a rigid dental model from a rigid negative mold difficult or impossible without damaging the model. By using a negative mold 2,4,18,50 that can be flexed, deformed, softened, fractured, or disassembled, the cast dental model can be released from the mold 2,4,18,50 without damage. Therefore, the use of the negative mold 2,4,18,50 that can be flexed, deformed, softened, fractured, or disassembled, overcomes an inherent difficulty in digitally forming rigid ceramic-based dental models typically used for fabricating orthodontic laboratory appliances.

Making a Physical Dental Model

Once the negative mold 2,4,18,50 has been formed using one of the methods described above, a physical dental model is made, as provided by block 112 in FIG. 1. In this step, a suitable model matrix material is cast in the negative mold 2,4,18,50. Preferably, the model matrix material does not shrink or expand significantly upon hardening and, once hardened, is heat resistant to allow fabrication of orthodontic laboratory appliances thereon. Optionally, the hardened model matrix material can handle localized temperatures exceeding 1970° C. that may be encountered during soldering, brazing and welding operations. In some embodiments, the model matrix material is orthodontic stone, such as plaster of Paris. However, other model matrix materials may be also be used, such as investment materials. Typical investment materials include gypsum or a refractory filler, such as silica in the form of cristobalite, quartz, leucite, zirconia, hafnia, zircon, alumina, magnesia, zircon, aluminosilicate, cordierite, mica, silicon nitride, silicon carbide, silica-alumina-nitrides, mullite, garnet, or mixtures thereof, in combination with a binder. Binders may include but are not limited to inorganic and organic binders, or mixtures thereof. Organic binders include, but are not limited to, polyvinyl pyrrolidine, polyvinyl alcohol, polyvinyl acetate, polyvinyl chloride, polyvinyl butryal and polystyrene, or mixtures thereof. Inorganic binders include, but are not limited to, magnesium oxide, ammonium phosphate, colloidal silica, calcium sulfate, magnesium phosphate, alkaline silicates, silica hydrosol, colloidal clays, or mixtures thereof.

If desired, a separation medium may be applied to the internal surfaces of negative mold 2,4,18,50 prior to casting the model matrix material in order to facilitate release of the hardened physical dental model. However, it is preferred that this layer is made as thin as possible, or that the thickness of this layer is compensated for when making the negative mold 2,4,18,50 since such a layer inherently reduces the size of the casting compared with that of the original dental structure.

Releasing the Physical Dental Model

After the model matrix material has hardened, at least two portions of the mold 2,4,18,50 are moved away from each other in order to release the physical dental model from the mold 2,4,18,50. This may be accomplished by fracturing or deforming the negative mold 2,4,50 as designated by block 114 of FIG. 1. If, however, the negative mold was prepared as an assembly of mold portions as shown in FIGS. 6 and 7, then the physical dental model may be released by disassembling the negative mold 18 as designated by block 116 of FIG. 1.

Figure 8:
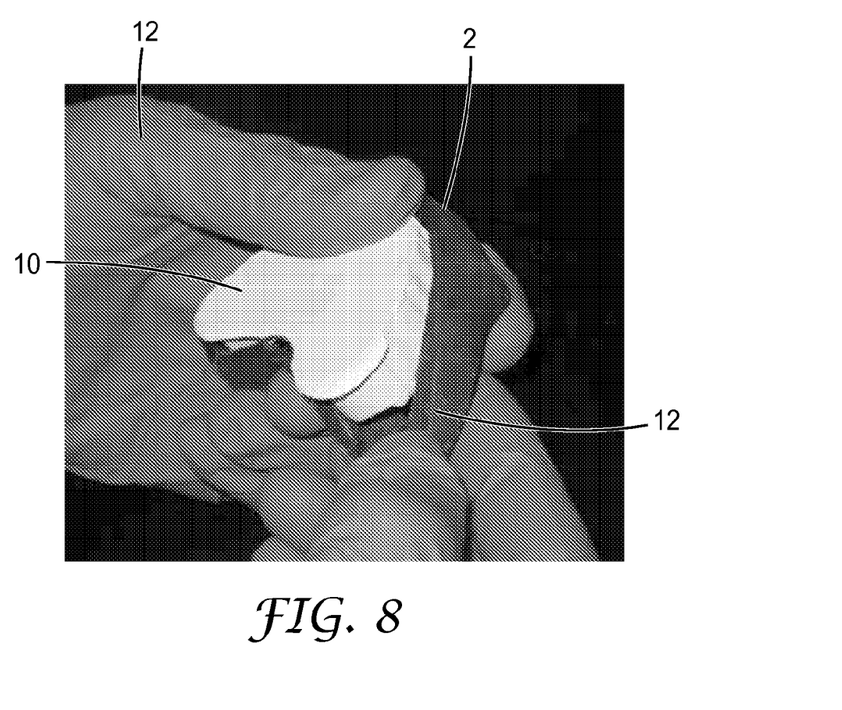
FIG. 8 shows the negative mold of FIGS. 3 and 4 being flexibly released from the positive dental model by a user.

An exemplary drawing of this process is shown in FIG. 8. In FIG. 8, the negative mold 2 is being released from a physical dental model 10 with a user's hand 12 assisting in deforming and stretching a wall of the negative mold 2 in a direction away from the physical dental model 10. A light tugging force may be simultaneously applied to fully disengage the physical dental model 10 from the negative mold 2. It is noted that any of the negative molds 2,4,18,50 exemplified may be released from a cast model in this fashion, provided that the mold 2,4,18,50 is formed from a suitably soft and flexible material. The physical dental model 10 should not normally be damaged during removal from the negative mold 2, even if the model 10 includes undercut regions that interlock or otherwise interfere with the negative mold 2.

If the negative mold 2,4,18,50 is too stiff to be easily removed from the physical dental model 10 at ambient temperature by deformation, then an additional softening or degradation step may be conducted prior to disengagement. Negative mold 2,4,18,50 may be softened or degraded by applying heat to the mold 2,4,18,50 through conduction, convection or radiation, in order to raise the temperature of the mold 2,4,18,50 above a softening or degradation point. In some embodiments, a softening point is a glass transition temperature. For example, if the negative mold 2,4,18,50 has a glass transition temperature of 40 degrees Celsius, it can be softened by bringing mold 2,4,18,50 into contact with a heating element, baking mold 2,4,18,50 in a convection oven, or irradiating mold 2,4,18,50 with infrared light to, for example, raise the temperature of the mold 2,4,18,50 to 60 degrees Celsius. It may be advantageous to use a mold 2,4,18,50 with a glass transition temperature above room temperature, since mold 2,4,18,50 can be stiff while casting model 10, and then soften "on demand" when heated above its glass transition temperature. Optionally, mold 2,4,18,50 may also be softened or degraded using a chemical means such as a suitable plasticizer or solvent or by chemically etching the mold 2,4,18,50 using a strong base such as sodium hydroxide. Alternatively, the mold 2,4,18,50 may also be degraded by photodegradation. For example, ultraviolet radiation may be used to induce polymer chain scission to degrade the negative mold 2,4,18,50. Other mechanical, thermal, or chemical methods may also be implemented to soften the negative mold 2,4,18,50, provided they do not adversely affect the physical dental model 10. Once the negative mold 2,4,18,50 has been sufficiently softened or degraded by any of the above methods, the mold 2,4,18,50 may be stretched or deformed to move at least two sections away from each other and facilitate release the physical dental model 10.

Figure 4:
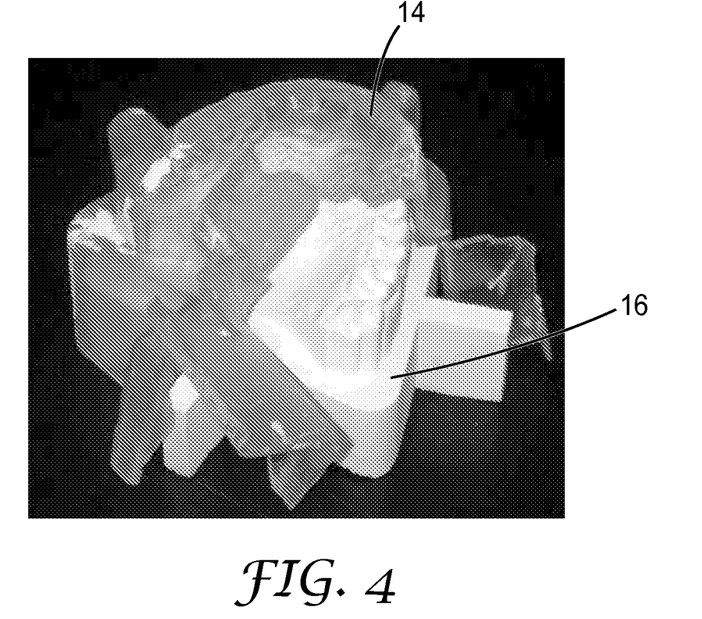
FIG. 4 shows a negative dental mold according to another embodiment of the invention being fractured from a physical dental model by a user.

Optionally and as shown in FIG. 4, a negative mold 14 is partially fractured to more easily separate mold 14 from a physical dental model 16. This is particularly appropriate if the mold 14 has notches, perforations, or grooves to assist in the fracturing process, as described earlier. Negative mold 14 may also be fully fractured into two or more separate distinct sections to further ease disengagement of mold 14 from the physical dental model 16. Again, it should be understood that these methods are not mutually exclusive of each other. For example, the negative molds 2,4,18,50 described in previous embodiments may also be partially or fully fractured to facilitate release of the molds 2,4,18,50 from the model 10.

In the embodiment shown in FIG. 7a, the support structure 52 may optionally be cut away, melted away, peeled away, or otherwise detached prior to releasing the physical dental model from the mold 50. By removing the support structure 52, the mold 50 is made more flexible, thereby facilitating release of the physical dental model. As a further option, the mold 50 may be notched, perforated, scored, or otherwise weakened, to define one or more lines of weakness along which the support structure 52 and the mold body 51 detach from each other. Alternatively, the support structure 52 and the mold body 51 may be formed from chemically dissimilar materials that inherently produce a weak interfacial boundary between them. The weak interfacial boundary thereby produces, in turn, lines of weakness along the seam 56 between the support structure 52 and mold body 51.

Fabricating an Orthodontic Laboratory Appliance

Once the plaster model has been prepared, an orthodontic laboratory appliance can be manufactured using the plaster model as designated by block 120 in FIG. 1. Presently, there are many established appliance providers, such as commercial orthodontic laboratories, that routinely use a stone model to fabricate laboratory appliances as a service to the orthodontic professional. This is one advantage of the present invention, since an infrastructure currently exists in the market for the manufacturing of laboratory appliances from physical dental models such as the models 10,16 in the embodiments exemplified above.

Figure 9:
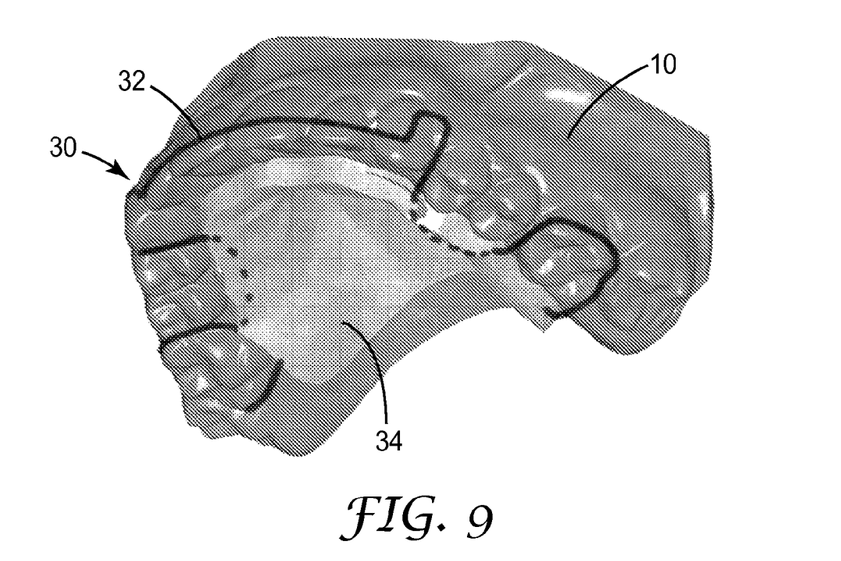
FIG. 9 shows an example of an orthodontic laboratory appliance being formed on a finished physical dental model.

FIG. 9 illustrates an exemplary laboratory appliance (in this case, a retainer). In this figure, an appliance 30 is formed on the physical dental model 10,16. Appliance 30 includes a wire portion 32 which contacts the model teeth along with a plastic body 34 that contacts the model palate. In some embodiments, wire portion 32 is made from metal, such as stainless steel, and conforms closely with the tooth portions of model 10,16. Wire portion 32 is partially embedded in a plastic body 34, which can be made from a cold-cured acrylic polymer such as polymethylmethacrylate. Body 34 may alternatively be made from a soft polymer such as a silicone or a thermoformed polymer such as polycarbonate.

To form appliance 30, wire portion 32 is first shaped to conform to model 10,16. The shaping of wire portion 32 is typically a manual process performed by a technician, but may also be automated using robotic wire bending techniques, such as those disclosed in U.S. Pat. No. 6,612,143 (Butscher et al), U.S. Pat. No. 6,928,733 (Rubbert et al) and U.S. Pat. No. 7,076,980 (Butscher). Furthermore, the plastic pads that conform to the soft tissues of the patient may be fitted by applying a layer of uncured acrylic resin on the model 10,16 to form the plastic body 34. Wire portion 32 may then be embedded in body 34 prior to curing body 34. Alternatively, a thermoformed polymer may be contacted with model 10,16 and heat and pressure applied to embed wires 32 and form body 34. Excess plastic on body 34 may then be trimmed as desired to provide the appliance 30. Optionally, the appliance 30 includes other components, including springs, customized frameworks, pivots, beams, and other mechanical elements. The above processes may also take into account the articulation of model 10,16 with an opposing lower dental model (not shown) to properly configure appliance 30.

Other laboratory appliances, such as Hyrax appliances, Twin Block, Crozat appliances and others, use open or closed loop wire configurations and optionally include appliance sections that are welded or brazed together on physical dental model 10,16. Other orthodontic laboratory appliances and appliance fabrication methods known to those of skill in the art are possible and examples are described in chapter 2-3, 2-6, and 2-7 of Willison, *Practical Guide to Orthodontic Appliances: a comprehensive resource from theory to fabrication*, Tonawanda, N.Y., Great Lakes Orthodontics, 2004, as well as issued U.S. Pat. No. 2,531,222 (Kesling), U.S. Pat. No. 3,271,858 (Simmons), U.S. Pat. No. 3,994,068 (Goshgarian), U.S. Pat. No. 4,798,534 (Breads) and U.S. Pat. No. 4,976,614 (Tepper).

Other Embodiments

The processes described in the foregoing may be entirely carried out within the office of an orthodontic professional. However, this need not be the case. In some embodiments, the digital data may be generated using a scanner at the office of an orthodontic professional or other service provider and then transmitted over the internet or some other electronic means to a remote location for processing. In some embodiments, the digital data is transmitted to a laboratory appliance fabricator.

Furthermore, the forming of the negative mold 2,4,14,18, preparation of the physical dental model 10,16, and fabrication of the laboratory appliance 30 may be completed in a remote location such as that of a laboratory appliance fabricator, after which the finished laboratory appliance is shipped back to the orthodontic professional. The physical dental model 10,16 may also be shipped back to the orthodontic professional if desired.

The management of digital data may be implemented in hardware or software, or a combination of the two. For example, software with a graphical interface may be employed to allow an orthodontic professional to configure and place an order for a laboratory appliance 30, approve billing and shipping information, and upload the digital data representing a patient's dentition to a laboratory appliance fabricator. Digital shape sampling and processing software may also be used to allow a technician of the fabricator to manipulate the digital data to configure the positive mold, negative mold 2,4,14,18, or negative mold sections 20,22,24, 26,28. For example, the software may enable the orthodontic professional to specify dimensions, shape, tooth surfaces of coverage, wire and loop sizes, and/or appliance material or stiffness. The techniques may be implemented in computer programs executing on programmable computers, where each computer includes a processor, a storage medium readable by the processor (including volatile and nonvolatile memory and/or storage elements), and suitable input and output devices. In some embodiments, the programmable computers are located at both the site of an orthodontic professional and at the site of a laboratory appliance provider.

Other embodiments are also possible. For example, the digital shape sampling and processing software described above may be used to analyze and compensate for material characteristics, such as shrinkage and expansion, of the materials that create the positive mold, negative mold 2,4,14,18, and physical dental model 10,16. The software and processing of the digital data may also be customized to the particular manufacturing methods used by the appliance fabricator.

EXAMPLES

The making of a physical dental model is further demonstrated by the following examples.

Example 1

Raw digital data, representing a patient's lower dental arch with surrounding soft tissue, was obtained from an intraoral scan provided by Brontes Technologies, Inc. (Lexington, Mass.). The digital data set was then cleansed and surfaced using Raindrop Geomagic software to produce a clear 3D surface image of the dental structure. This surface was then offset to define a negative shell with an interior contour exactly matching the original dental structure. The negative shell, as represented by the digital data, was then printed using a VIPER brand SLA system from 3D Systems using ACCURA brand Si-40 photopolymer SLA material, also from 3D Systems. The printed negative shell was then used as a mold to cast a positive dental model using white orthodontic stone provided by Whip-Mix Corporation (Louisville, Ky.). Once cast, the stone model was allowed to set at room temperature for 1 hour. After the stone model was fully hardened, the negative mold and stone dental model were placed in an oven at 150 degrees Celsius for 15 minutes. The mold was then removed from the oven peeled away in sections. All features on the stone model were observed to be accurate and undamaged.

Example 2

The original digital data set from Example 1 was then used to print a second negative shell, this time using a low modulus resin. To form the low modulus shell, the digital data set was again refined and offset to produce a virtual digital shell structure. A physical shell based on the virtual shell was then printed using an EDEN 500V 3D printing machine from Objet Geometries, used with Fullcure 930 Series "Tango-Black" resin, also provided by Objet Geometries. To provide added strength, the shell thickness for this prototype was defined to be approximately 3 millimeters. Once again, the printed shell was used as a negative mold to cast a positive dental model using orthodontic stone as described in Example 1. After the model had set, the negative mold was flexibly removed from the cast stone dental model at room temperature with no apparent damage to the cast model. This example demonstrates that a rapid prototyping process can directly fabricate a negative mold that is sufficiently flexible to disengage from complex undercut dental structures at room temperature.

Example 3

As in Example 1, a digital data set representing a dental structure was cleansed and surfaced. Instead of using the surface to define a negative mold object, however, the data set was used to define a virtual positive mold object or a replica of the dental structure. This data set was then used to print a positive mold using the VIPER brand SLA system and ACCURA brand Si-40 photopolymer SLA material mentioned above. After verifying the positive mold was accurate, a negative mold was formed over the positive mold using Z-DUPE brand duplication silicone provided by Henry-Schein Inc. (Melville, N.Y.) in conjunction with a cylindrical molding vessel, fully submerging the positive mold in the Z-DUPE material, and allowing the silicone to set for 2 hours. After the silicone negative mold was hardened, it was detached from the positive mold and subsequently used to cast the physical dental model out of orthodontic stone as carried out in Examples 1 and 2. The Z-DUPE matrix material was observed to be highly elastic and easily separated from the stone dental model after 1 hour. The final stone model was substantially free of defects and displayed an adequate surface finish.

The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

The invention claimed is:

1. A method of producing an orthodontic laboratory appliance comprising:
   obtaining digital data representing at least a portion of a patient's dental structure;
   forming a negative mold replicating the contours of at least some of the dental structure by using the digital data to directly print the negative mold by rapid prototyping;
   making a physical dental model from the negative mold;
   moving at least two sections of the negative mold away from each other in order to release the physical dental model from the negative mold; and
   fabricating the laboratory appliance from the physical dental model.

2. The method of claim 1, wherein the act of moving at least two sections of the negative mold away from each other is carried out while the temperature of the negative mold is above ambient temperature.

3. The method of claim 2, wherein the act of forming a negative mold is carried out by forming the negative mold from a polymer resin with a glass transition temperature above room temperature.

4. The method of claim 1, wherein the act of moving at least two sections of the negative mold away from each other includes the act of fracturing the negative mold.

5. The method of claim 1, wherein the act of moving at least two sections of the negative mold away from each other includes of the act of chemically degrading the negative mold.

6. The method of claim 1, wherein the act of moving at least two sections of the negative mold away from each other includes the act of stretching the negative mold.

7. The method of claim 1, wherein the negative mold comprises a support structure.

8. The method of claim 7, further comprising detaching the support structure from the negative mold prior to moving at least two sections of the negative mold away from each other.

9. The method of claim 7, wherein the negative mold is formed from a first material and the support structure is formed from a second material that has a Shore hardness different from the first material.

10. The method of claim 1, wherein the act of forming the negative mold is carried out by forming the negative mold from a resin material with a Shore Scale A hardness that is in the range of 2 to 90.

11. The method of claim 1, and including the act of aligning the at least two mold sections with each other using at least one coupling pin that extends through at least a portion of the negative mold.

12. The method of claim 1, wherein the act of forming the negative mold includes the act of providing at least one line of weakness in the negative mold to facilitate separating the negative mold from the physical dental model.

13. The method of claim 1, wherein the act of obtaining digital data is carried out using an intraoral scanner.

14. The method of claim 1, wherein the act of making physical dental model includes the act of making the physical dental model using orthodontic stone.

15. The method of claim 1, wherein the act of forming a negative mold is carried out by forming the negative mold with an average wall thickness in the range of 0.25 millimeters to 10 millimeters.

* * * * *